United States Patent
Wang et al.

(10) Patent No.: US 8,750,586 B2
(45) Date of Patent: Jun. 10, 2014

(54) METHOD AND APPARATUS FOR QUANTITATIVE IMAGING OF BLOOD PERFUSION IN LIVING TISSUE

(75) Inventors: Ruikang Wang, Portland, OR (US); Lin An, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 315 days.

(21) Appl. No.: 13/318,737

(22) PCT Filed: May 4, 2010

(86) PCT No.: PCT/US2010/033462
§ 371 (c)(1),
(2), (4) Date: Nov. 3, 2011

(87) PCT Pub. No.: WO2010/129494
PCT Pub. Date: Nov. 11, 2010

(65) Prior Publication Data
US 2012/0063665 A1    Mar. 15, 2012

Related U.S. Application Data

(60) Provisional application No. 61/175,229, filed on May 4, 2009.

(51) Int. Cl.
*G06T 7/00* (2006.01)
(52) U.S. Cl.
USPC .......................................... 382/130; 600/479
(58) Field of Classification Search
CPC .................. G06T 7/0012; G06T 2207/10101; G06T 2207/30104; A61B 5/0033; A61B 5/0066; A61B 5/0261; G01B 9/02083; G01B 9/02091; G01N 21/4795; G01N 2021/1787; G01N 2021/4795; G01N 2021/49; G01N 2021/53
USPC ........... 382/100, 128, 130; 128/922; 600/310, 600/425, 473, 476, 479
See application file for complete search history.

(56) References Cited

U.S. PATENT DOCUMENTS

| | | | |
|---|---|---|---|
| 4,131,022 A | 12/1978 | Mezrich | 73/606 |
| 6,549,801 B1 | 4/2003 | Chen et al. | 600/425 |
| 2003/0199769 A1 | 10/2003 | Podoleanu et al. | 600/476 |
| 2003/0199796 A1 | 10/2003 | Yamazaki et al. | 601/87 |
| 2003/0220749 A1 | 11/2003 | Chen et al. | 702/31 |
| 2005/0004453 A1 | 1/2005 | Tearney et al. | 600/427 |
| 2005/0140984 A1 | 6/2005 | Hitzenberger | 356/497 |
| 2005/0171438 A1 | 8/2005 | Chen et al. | 600/476 |
| 2005/0253055 A1 | 11/2005 | Sprague et al. | 250/234 |
| 2006/0270929 A1 | 11/2006 | Bouma et al. | 600/407 |
| 2009/0225324 A1 | 9/2009 | Bernstein et al. | 356/479 |
| 2009/0226096 A1 | 9/2009 | Namai et al. | 382/199 |
| 2010/0027857 A1 | 2/2010 | Wang | 382/128 |
| 2012/0307014 A1 | 12/2012 | Wang | 348/46 |

FOREIGN PATENT DOCUMENTS

| | | | | |
|---|---|---|---|---|
| WO | WO2004043245 A1 | 5/2004 | | G01N 21/47 |
| WO | WO2008039660 A2 | 4/2008 | | A61B 3/12 |
| WO | WO2011097031 A2 | 8/2011 | | A61B 3/18 |

OTHER PUBLICATIONS

An, Lin et al., "In Vivo Volumetric Imaging of Vascular Perfusion Within Human Retina and Choroids with Optical Micro-angiography," Optics Express, 2008, vol. 16, No. 15, pp. 11438-11452.
Wang, Ruikang K. et al., "Doppler Optical Micro-angiography for Volumetric Imaging of Vascular Perfusion in Vivo," Optics Express, 2009, vol. 17, pp. 8926-8940.
An, Lin et al., "Ultrahigh Sensitive Optical Microangiography for in vivo Imaging of Microcirculations Within Human Skin Tissue Beds," Optics Express, 2010, vol. 18, No. 8, pp. 8220-8228.
Yasuno, Y. et al,"Simultaneous B-M-Mode Scanning Method for Real-Time Full-Range Fourier Domain Optical Coherence Tomography," Applied Optics, OSA, Optical Society of America, 2006, pp. 1861-1865.
Wojtkowski, M. et al., "Real-time in Vivo Imaging by High-speed Spectral Optical Coherence Tomography," Optics Letters, OSA, Optical Society of America, 2003, vol. 28, No. 19, pp. 1745-1747.
Wojtkowski, M. et al., "In Vivo Human Retinal Imaging by Fourier Domain Optical Coherence Tomography," Journal of Biomedical Optics, SPIE, 2002, vol. 7, No. 3, pp. 457-463.
Shuliang, J. et al., "Simultaneous Acquisition of Sectional and Fundus Ophthalmic Images with Spectral-domain Optical Coherence Tomography," Optics Express, 2005, vol. 13, No. 2, pp. 444-452.
Sarunic, Marinko V. et al., "Real-time Quadrature Projection Complex Conjugate Resolved Fourier Domain Optical Coherence Tomography," Optics Letters, 2006, vol. 31, pp. 2426-2428.
Vakoc, B.J. et al., Elimination of Depth Degeneracy in Optical Frequency-domain Imaging Through Polarization-based Optical Demodulation, Optics Letters, 2006, vol. 31, pp. 362-364.

(Continued)

*Primary Examiner* — Andrew W Johns
(74) *Attorney, Agent, or Firm* — Schwabe, Williamson & Wyatt

(57) ABSTRACT

Embodiments provide methods and systems for quantitative imaging of blood perfusion in living tissue. A method provides for obtaining an optical microangiography (OMAG) image of a sample, wherein the image has an OMAG background sample; digitally reconstructing a homogeneous ideal static background tissue; replacing the OMAG background sample with the digitally reconstructed homogeneous ideal static background tissue; correlating two or more neighboring A-lines with the digitally reconstructed homogeneous ideal static background tissue; and measuring a phase difference between the two or more neighboring A-lines to quantify blood perfusion in the sample. Methods using digital reconstruction to reduce random phase noise in phase-resolved Doppler OCT are also provided.

23 Claims, 8 Drawing Sheets

(56) References Cited

OTHER PUBLICATIONS

Bachmann, Adrian H. et al., "Heterodyne Fourier Domain Optical Coherence Tomography for Full Range Probing with High Axial Resolution," Optics Express, 2006, vol. 14, No. 4, pp. 1487-1496.

Ma, Zhen et al., "Arbitrary Three-phase Shifting Algorithm for Achieving Full Range Spectral Optical Coherence Tomography," Chinese Physics Letters, 2006, vol. 23, No. 2, pp. 366-369.

Yasuno, Yoshiaki, et al., "Real Time and Full-Range Complex Fourier Domain Optical Coherence Tomography," Optical and Quantum Electronics, 2005, vol. 37, Nos. 13-15, pp. 1157-1163.

Sarunic, Marinko et al., "Instantaneous Complex Conjugate Resolved Spectral Domain and Swept-source OCT Using 3x3 Fiber Couplers," Optics Express, 2005, vol. 13, pp. 957-967.

Huber, R., et al., "Amplified, Frequency Swept Lasers for Frequency Domain Reflectometry and OCT Imaging: Design and Scaling Principles," Optics Express, 2005, vol. 13, No. 9, pp. 3513-3528.

Gotzinger, Erich et al., "High Speed Full Range Complex Spectral Domain Optical Coherence Tomography," Optics Express, 2005, vol. 13, No. 2, pp. 583-594.

Zhang, Jun, et al., "Full Range Polarization-sensitive Fourier Domain Optical Coherence Tomography," Optics Express, 2004, vol. 12, No. 24, pp. 6033-6039.

Yun, S., et al., "Removing the Depth-degeneracy in Optical Frequency Domain Imaging with Frequency Shifting," Optics Express, 2004, vol. 12, pp. 4822-4828.

Wojtkowski, M. et al., "Full Range Complex Spectral Optical Coherence Tomography Technique in Eye Imaging," Optics Letters, 2002, vol. 27, No. 16, pp. 1415-1417.

Leitgeb, Rainer A. et al., "Phase-shifting Algorithm to Achieve High-speed Long-depth-range Probing by Frequency-domain Optical Coherence Tomography," Optics Letters, 2003, vol. 28, No. 22, pp. 2201-2203.

Hitzenberger, Christoph K., et al., "Differential Phase Measurements in Low-Coherence Interferometry Without 2 pi Ambiguity," Optics Letters, 2001, vol. 26, No. 23, pp. 1864-1866.

Choma, Michael A., et al., "Doppler Flow Imaging of Cytoplasmic Streaming Using Spectral Domain Phase Microscopy," Journal of Biomedical Optics, 2006, vol. 11, No. 2, Article No. 024014.

Seki, J. et al., "Velocity Profiles in the Rat Cerebral Microvessels Measured by Optical Coherence Tomography," Clinical Hemorheology and Microcirculation, 2006, vol. 34, Nos. 1-2, pp. 233-239.

Leitgeb, Rainer A. et al., "Real-time Measurement of In Vitro Flow by Fourier-domain Color Doppler Optical Coherence Tomography," Optics Letters, 2004, vol. 29, No. 2, pp. 171-173.

Leitgeb, Rainer A. et al., "Real-time Assessment of Retinal Blood Flow with Ultrafast Acquisition by Color Doppler Fourier Domain Optical Coherence Tomography," Optics Express, 2003, vol. 11, No. 23, pp. 3116-3121.

Ahn, Yeh-Chan, et al., "Investigation of Laminar Dispersion with Optical Coherence Tomography and Optical Doppler Tomography," Optics Express, 2005, vol. 13, No. 20, pp. 8164-8171.

Zhang, Jun et al., "In Vivo Blood Flow Imaging by a Swept Laser Source Based Fourier Domain Optical Doppler Tomography," Optics Express, 2005, vol. 13, No. 19, pp. 7449-7457.

Pedersen Cameron J., et al., "Phase-referenced Doppler Optical Coherence Tomography in Scattering Media," Optics Letters, 2005, vol. 30, No. 16, pp. 2125-2127.

Vakoc, B.J., et al., "Phase-resolved Optical Frequency Domain Imaging," Optics Express, 2005, vol. 13, No. 14, pp. 5483-5493.

Wang, Ruikang K., "Three-dimensional Optical Micro-angiography Maps Directional Blood Perfusion Deep Within Microcirculation Tissue Beds In Vivo," Physics in Medicine and Biology, 2007, vol. 52, N531-N537.

Wang, Ruikang K. et al., "Three Dimensional Optical Angiography," Optics Express, 2007, vol. 15, No. 7, pp. 4083-4097.

METHOD AND APPARATUS FOR QUANTITATIVE IMAGING OF BLOOD PERFUSION IN LIVING TISSUE

CROSS REFERENCE TO RELATED APPLICATIONS

The present application claims priority to U.S. Provisional Patent Application No. 61/175,229, filed May 4, 2009, entitled "Method and Apparatus for Quantitative Imaging of Blood Perfusion in Living Tissue," the disclosure of which is hereby incorporated by reference in its entirety.

The present application is related to International Publication No. WO2008/039660, filed Sep. 18, 2007, entitled "In Vivo Structural and Flow Imaging," the disclosure of which is hereby incorporated by reference in its entirety.

GOVERNMENT INTERESTS

This invention was made with Government support under Grant No. R01HL093140 from the National Heart, Lung, and Blood Institute, and Grant No R01 EB009682 from the National Institute of Biomedical Imaging and Bioengineering. The Government has certain rights in the invention.

TECHNICAL FIELD

Embodiments herein relate to imaging, and, more specifically, to a method and apparatus for quantitative imaging of blood perfusion in living tissue.

BACKGROUND

In vivo, three-dimensional mapping of biological tissues and vasculature is challenging because of the highly-scattering and -absorptive nature of such tissues. Optical coherence tomography (OCT) is a non-invasive imaging technology that is capable of providing high resolution, depth-resolved cross-sectional images of highly scattering samples. In addition, phase-resolved Doppler OCT (PRDOCT), a functional extension of OCT, may be used to extract velocity information about blood flow in functional vessels within the scanned tissue beds by evaluating phase differences between neighboring A-lines in an OCT B-scan frame. Recent developments in the imaging speed and sensitivity of spectral domain optical coherence tomography (SDOCT) have allowed PRDOCT to be used for in vivo imaging of blood flow, particularly in human retina. In spectral domain PRDOCT, the magnitude of Fourier transformation of the spectral interference fringes is used to reconstruct cross-sectional, structural images of the tissue sample, while the phase difference between neighboring A-scans is used to extract the velocity information of blood flow within the scanned tissue. The phase resolved method is based on the fact that the phase difference of sequential A-lines is linearly related to the flow velocity; thus, the PRDOCT method may be used to obtain quantitative information about the blood flow.

Although the PRDOCT method is of high resolution and high sensitivity to the blood flow, its imaging performance is greatly deteriorated by at least two factors: 1) the characteristic texture pattern artifact, which is caused by optical heterogeneity of the sample, and 2) the phase instability that is caused by the sample motion artifacts. The background characteristic texture pattern may be reduced in PRDOCT by using a dense-sampling approach, e.g., using more A-scans within a B-scan. This dense-sampling approach is effective in reducing the texture pattern artifacts, but it inevitably leads to a significant increase of imaging time, which is undesirable for in vivo imaging applications.

Resonant Doppler imaging may be used to minimize the influence of phase instabilities by extracting the flow information from the intensity signals without extracting the phase. Alternatively, joint spectral and time domain OCT may be used to rely on analyses of the amplitude and phase distributions of the OCT signals. However, these methods require repeated A-scans at the same lateral position, which increases the imaging time.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

FIG. 4A shoes an OMAG structural image, FIG. 4B shows an OMAG flow image, FIG. 4C shows a DOMAG velocity image, FIG. 4D shows a PRDOCT velocity image, and FIG. 4E shows flow signal profiles extracted from the positions marked in FIG. 4C and FIG. 4D, in accordance with various embodiments;

FIG. 5A shows an OMAG image of microstructures, identical to a conventional SDOCT image, FIG. 5B shows the corresponding OMAG image of blood flow, and FIG. 5C shows the corresponding DOMAG image of velocities of the blood flow, in accordance with various embodiments;

FIG. 8A) and the corresponding OMAG flow image (FIG. 8B), DOMAG flow velocity image (FIG. 8C), and PRDOCT flow velocity image (FIG. 8D), in accordance with various embodiments;

FIG. 10A shows a conventional PRDOCT flow image without segmentation, FIG. 10B shows a conventional PRDOCT flow image with segmentation; and FIG. 10C shows a Doppler OMAG flow image, in accordance with various embodiments;

FIG. 12A shows a FDOCT structure image; FIG. 12B shows a phase-only filtering flow image; and FIG. 12C shows a phase-only filter DOMAG image of velocities of blood flow, in accordance with various embodiments.

DETAILED DESCRIPTION OF DISCLOSED EMBODIMENTS

Figure 1A:
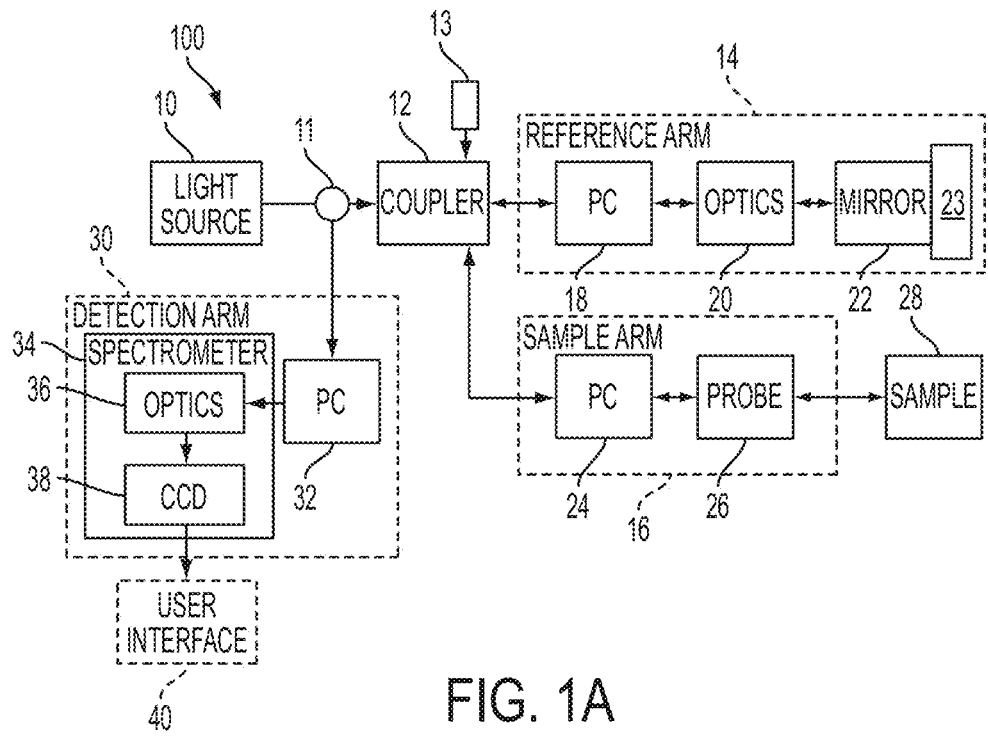
FIGS. 1A and 1B illustrate a flow diagram (FIG. 1A) and a schematic diagram (FIG. 1B) of an exemplary optical microangiography (OMAG) system that may be used to image the velocities of blood flow, in accordance with various embodiments.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the phrases "in an embodiment," or "in embodiments," which may each refer to one or more of the same or different embodiments. Furthermore, the terms "comprising," "including," "having," and the like, as used with respect to embodiments, are synonymous.

In various embodiments, methods, apparatuses, and systems for quantitative imaging of blood perfusion in living tissue are provided. In exemplary embodiments, a computing device may be endowed with one or more components of the disclosed apparatuses and/or systems and may be employed to perform one or more methods as disclosed herein.

Embodiments herein provide methods and apparatus for the quantitative assessment of blood flow and perfusion in living tissue at the capillary level of resolution. In embodiments, parameters that may be measured include the blood flow rate in individual blood vessels, the blood flow perfusion rate within a scanned tissue volume, measurement of blood vessel diameters (inner diameter), blood vessel density within a scanned tissue volume, and vessel tortuosity. Embodiments also may provide digital reconstruction of the tissue background to address background noise and enhance imaging results.

The disclosed embodiments may be used in a variety of applications, such as the optical coherence tomography imaging of human retina. Other applications include a wide range of clinical and research areas having vascular involvement, such as cancer, neurovascular diseases, diabetes, eye diseases, ear diseases, cardiovascular diseases, skin diseases, as well as in small animal studies, and the like.

Various embodiments provide a novel imaging technique called Doppler optical microangiography (DOMAG) that permits quantitative imaging of blood perfusion in living tissue. Unlike the phase-resolved Doppler OCT (PRDOCT) method, optical microangiography (OMAG) utilizes implicitly the phase information embedded in the OCT spectral interferograms. In embodiments, OMAG uses heterodyne technology to separate (a) the scattering signals caused by the moving scatters, from (b) the scattering signals caused by the static tissue background (e.g., the tissue microstructures). In addition to its ability to achieve micro-structural imaging, OMAG provides volumetric vasculature imaging within a scanned tissue bed at capillary-level resolution. In embodiments, OMAG may be used to image, for instance, cerebral blood perfusion and blood flow within human retina and choroid. In some embodiments, an advantage of OMAG is that only the signals backscattered by the functional blood appear in the OMAG flow output plane, making blood flow imaging substantially free of artifact-induced noise.

For the purposes of describing embodiments of the disclosure, the term "A-line" or "A-scan" refers to an axial scan (a line along the depth or z axis direction). The term "B-line" or "B-scan" refers to a collection of a number of A-scans captured when a probe beam scans over a sample in the lateral or x direction. "C-scan" refers to a collection of a number of B-scans captured when the probe beam scans over a sample in an elevational or y direction.

As described herein, DOMAG may be used in some embodiments to evaluate the velocities of OMAG flow signals by measuring the phase difference between neighboring A-lines. In embodiments, the method may use a PRDOCT approach to evaluate the phase difference between neighboring OMAG A-lines, however, the application of the phase-resolved technique may require a correlation between neighboring A-scans. This correlation requirement may make extraction of the blood flow velocities in OMAG difficult because in the OMAG flow image, the regions that are occupied by the microstructural signals are rejected by OMAG, which may lead to a loss of the correlation between neighboring A-scans in these regions.

In embodiments, to overcome this problem, an ideal static background tissue may be digitally reconstructed that is totally optically homogeneous to replace the real heterogeneous tissue sample in OMAG. This ideal background tissue may provide a constant background signal that makes the neighboring A-scans totally correlated, which may lead to a dramatic increase in the phase signal to noise ratio (SNR) for the phase-resolved signals that represent flow velocities.

FIG. 1A illustrates an exemplary embodiment of an optical microangiography (OMAG) system 100 that may be used to image the velocities of blood flow.

The illustrated OMAG system 100 may include some features known in the art, features which may not be explained in great length herein except where helpful in understanding embodiments of the present disclosure.

As illustrated, the OMAG system 100 includes a light source 10. The light source 10 may be any light source suitable for the purpose, including, but not limited to, a broadband light source or a tunable laser source. A suitable broadband light source may include a superluminescent diode. In one embodiment, the light source 10 may comprise a superluminescent diode (for instance, from DenseLight, Singapore) with a central wavelength of 1310 nanometers (nm) and a spectral bandwidth of 56 nm, which may provide an axial imaging resolution of about 13 micrometers (μm) in air. In various embodiments, the light source 10 may be a light source having shorter or longer wavelengths, or may provide more than one wavelength. In various other embodiments, light source 10 may comprise a tunable laser source such as, for example, a swept laser source.

Figure 1B:
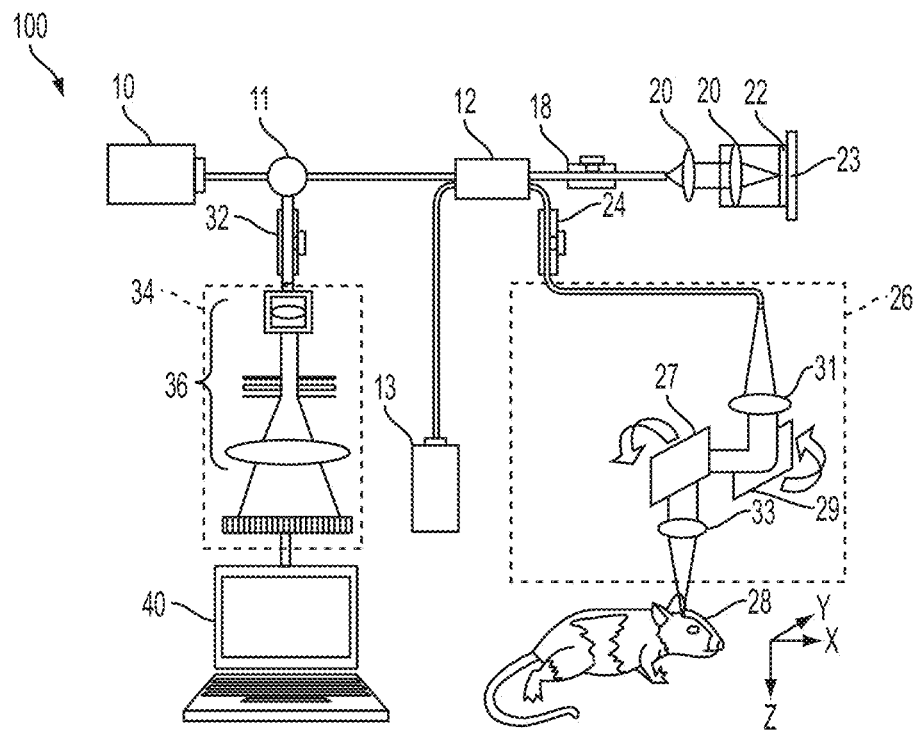

The OMAG system 100 includes a fiber coupler 12 for splitting the light from light source 10 into two beams: a first beam provided to a reference arm 14 and a second beam provided to a sample arm 16. In various embodiments, fiber coupler 12 may comprise a 2×2 fiber coupler or any fiber coupler suitable for the purpose. In particular embodiments, the light from light source 10 may be coupled into a fiber-based interferometer (for example a Michelson interferometer) via an optical circulator 11 (see, e.g., FIG. 1B) prior to being routed to fiber coupler 12. Further embodiments also may include a laser diode 13 (see, e.g., FIG. 1B), for instance a 633 nm laser diode, that may couple to fiber coupler 24.

Sample arm 16 may be configured to provide light from light source 10 to a sample 28 by way of a polarization controller 24 and a probe 26. Probe 26 includes a scanning device (for example a pair of x-y galvanometer scanners 27, 29) (see, e.g., FIG. 1B) for scanning the probe beam over sample 28 in the x and y directions. Probe 26 also comprises the appropriate optics, such as a collimating lens 31 and/or an objective lens 33 (see, e.g., FIG. 1B) for delivering the light onto sample 28. In various embodiments, probe 26 also receives backscattered light from sample 28. Although the characteristics of the light provided to sample 28 may depend on the particular application, in some embodiments, for instance with a 50 mm focal length of the objective lens, the lateral imaging resolution may be approximately 16 μm, which may be determined by an objective lens that focuses light onto sample 28, with a light power on sample 28 being approximately 1 milliwatt (mW).

Reference arm 14 may be configured to provide a reference light to a detection arm 30 (discussed more fully below), from the light provided by light source 10, for producing a spectral interferogram in combination with backscattered light from sample 28. Reference arm 14 includes optics 20 and a mirror 22 for reflecting light from light source 10 in order to provide the reference light. Optics 20 may include, but are not limited to, various lenses suitable for the purpose, for instance a collimating lens and/or an objective lens (not shown). In embodiments, the zero delay line of the system may be set at about 0.5 mm above the focus spot of sample 28.

Mirror 22 may be stationary or may be modulated by a modulator 23. Modulation may be equivalent to frequency modulation of the detected signal at the detection arm 30. In embodiments, spectral interference signals (interferograms) may be modulated by a constant Doppler frequency, $\omega_0$, by a modulated mirror 22 in reference arm 14, the modulation making it feasible to separate the moving and static components within sample 28. The spectral interference signal may then be recovered by de-modulating the modulated signal at the modulation frequency, $\omega_0$. De-modulation may be achieved using any suitable method including, for example, a digital or optical de-modulation method. In embodiments, modulation and de-modulation of spectral interference signals may advantageously improve the signal-to-noise ratio, resulting in an improved image quality for structural, flow, and angiographic imaging.

Various methods may be used for modulating mirror 22. For example, in various embodiments, modulator 23 may be a linear piezo-translation stage onto which mirror 22 is mounted. The piezo-translation stage may be configured to move mirror 22 at some constant velocity across a B-scan (e.g., the x direction scan). In an exemplary embodiment, mirror 22 is mounted onto a piezo-translation stage driven by a 10 Hz saw-tooth waveform with an amplitude of 50 μm. In various other embodiments, however, modulator 23 may be a phase-modulating device (e.g., an electro-optic phase modulator or acoustic phase modulator) or another suitable device for introducing a suitable Doppler frequency modulation. In various embodiments, the optical path-length in the reference arm or in the sample arm may be modulated which has the same or similar effect as moving mirror 22 back and forth at a constant speed. In an embodiment, a method of stretching the optical fiber may be used. In various embodiments, the modulation of the interferogram may also be provided by probe 26. In an exemplary embodiment, probe 26 may be configured such that the input signal is scanned with an offset reference to the pivot point.

In various embodiments, modulation may be simply provided by the moving particles, for example the flowing blood cells in the patent vessel within tissue sample. In this case, the reference mirror 22 may be stationary.

The light returning from reference arm 14 and the light returning from sample arm 16 (e.g., the spectral signal) may be recombined and coupled into a single mode fiber by a coupler 12 for introduction to a detection arm 30. As illustrated, detection arm 30 includes a spectrometer 34 and one or more of various optics 36 including, but not limited to, one or more collimators, one or more diffracting/transmission gratings, and one or more lenses (not illustrated). In exemplary embodiments, optics 36 may include a 30-millimeter (mm) focal length collimator, a 1200 lines/mm diffracting grating, and an achromatic focusing lens with a 100 mm focal length. Such parameters are exemplary and may be modified in a variety of ways in accordance with the embodiments disclosed herein.

In embodiments employing a broadband light source, spectrometer 34 may include a detector array such as a charge-coupled device (CCD) 38 configured to detect a spectral interference signal. CCD 38 may include one or more of a line-scan camera and an area scan camera. An exemplary suitable CCD 38 may be a CCD consisting of a 14-bit, 1024 pixel InGaAs line scan camera. In one specific example, the maximum line scan rate of the camera may be about 47 KHz, and the spectrometer setup may have a designed spectral resolution of about 0.141 nm, which may give a measured imaging depth of about 3.0 mm on each side of the zero delay line. For those embodiments wherein light source 10 comprises a tunable laser rather than a broadband light source, however, OMAG system 100 may include a diffusion amplifier that may comprise one or more single element detectors rather than a spectrometer 34. For example, one or more dual-balanced photo-diode detectors may be used.

As illustrated, reference arm 14, sample arm 16, and detection arm 30 include polarization controllers 18, 24, and 32, respectively. Polarization controllers 18, 24, 32 may be configured to fine-tune the polarization states of light in the OMAG system 100. Although an OMAG system within the scope of the present disclosure may include more or fewer polarization controllers than illustrated, the provision of polarization controllers 18, 24, and 32 in reference arm 14, sample arm 16, and detection arm 30, respectively, may advantageously maximize the spectral interference fringe contrast at the CCD 38 (or other suitable detector).

In various embodiments, OMAG system 100 includes one or more user interfaces 40 for one or more purposes including displaying images, input of data, output of data, etc.

OMAG system 100 may be configured to build a 3-D data volume set by scanning sample 28 with a sample light in x, y, and λ (z) directions to obtain a 3-D spectral interferogram data set. In exemplary embodiments, probe 26 may be scanned in the lateral direction (x direction) by an x-scanner and in the elevational direction (y direction) by a y-scanner. In various embodiments, the x-scanner may be driven by a 10 Hz saw-tooth waveform with an amplitude equivalent to 2.2 mm, and the y-scanner may be driven at 0.02 Hz with an amplitude of 2.2 mm. In embodiments, this configuration may determine a line scan rate of about 31 KHz for the camera. In this same specific, non-limiting example, the imaging rate may be set at 20 frames (B-scan) per second (fps), and each B-scan may have a 2.5 mm span over the sample, including 1500 A-lines. In embodiments, this may represent an over sampling factor of about 10 because the lateral resolution of the system may be about 16 µm. In this example, in the elevational direction, there may be 500 discrete points along about 2.5 mm, e.g., 500 B-scans. Hence, the data cube of each 3D image (C-scan) in this exemplary embodiment may be composed of 1024 by 1500 by 500 (z-x-y) voxels, which may take about 25 seconds to acquire. In specific examples, the operations for probe beam scanning, data acquisition, data storage and hand-shaking between them may be controlled by a custom software package written, for example, in C++ language. In this example, 500 B-scans for a C-scan represented over sampling in the elevational direction. In practice, however, 200 B-scans may be sufficient to obtain the volumetric images, leading to a temporal resolution of about 10 seconds for 3D OMAG imaging.

As discussed above, the DOMAG method may use the OMAG method to obtain optical signals, for instance optical signals backscattered by blood cells in blood vessels, through rejecting the heterogeneous tissue signals, e.g., the optical signals backscattered by microstructures of the tissue sample. In embodiments, the method may then use a phase resolved DOCT technique to extract the flow velocity information. At first glance, applying the phase-resolved technique to extract flow velocities from OMAG signals of blood flow may appear straightforward. However, the technique assumes a correlation between neighboroing OCT A-scan signals. In various embodiments, such a correlation is not achievable in the background tissue regions in OMAG, making the extraction of flow velocities difficult. In embodiments, the DOMAG method described herein may circumvent this difficulty.

In various embodiments, the spectral interference signal captured by each pixel of the CCD camera in OMAG/SDOCT is essentially the same except for the wavelength, λ. In embodiments, the method assumes that the wavenumbers of the broad band light source is from $k_0$ to $k_0+\Delta k$, where $k_0=2\pi/\lambda_0$, and these wavenumbers cover 1024 pixels of the line scan camera. As a consequence, the camera may record the spectral interference fringe signal formed between the reference light and the light backscattered from within sample, which may be written as a function of kj:

$$I(k_j)=S(k_j)\left\langle |E_R\exp(i2k_jr)+\int_{-\infty}^{\infty}a(z)\exp\{i2k_j[r+nz]\}dz|^2\right\rangle \quad j=1,2,3\ldots 1024 \quad (1)$$

where $i=\sqrt{-1}$, $<>$ is the time average, $k_j$ is the wavenumber of the light captured by the jth detector (pixel) of the CCD camera, $I(k_j)$ is the light intensity captured by the jth detector, $S(k_j)$ is the spectral density of the light source at $k_j$, r is the optical path length for the light traveled in the reference arm, n is the refractive index of the sample, a(z) is the magnitude of the light backscattered at depth z. $E_R$ represents the magnitude of the reference light. In this embodiment, each B-scan may contain 1500 A-lines and covers about 2.5 mm in the lateral direction. So the signal captured by the jth pixel in each B-scan may be written as a function of the time variable t that relates to the position of the focus beam spot on the sample, steered by the X scanning mirror.

$$I(k_j,t)=S(k_j)\left\langle |E_R\exp(i2k_jr)+\int_{-\infty}^{\infty}a(z,t)\exp\{i2k_j[r+nz]\}dz|^2\right\rangle \quad (2)$$

In embodiments, because the light backscattered from the sample is quite weak compared to the light reflected from the reference mirror, the self cross-correlation between the light backscattered from different positions within the sample is not considered. The DC signals are also not considered in various embodiments because they do not contribute to useful OMAG signals. In these cases, Eq. (2) may be written as:

$$I(k_j,t)=2S(k_j)E_R\int_{-\infty}^{\infty}a(z,t)\cos(2k_jnz)dz \quad (3)$$

It is clear that Eq. (3) is constant if the sample is totally optically homogeneous, which means that a(z,t) and n do not vary within the entire sample. In embodiments, if this is the case, then the spatial frequency components of the sample in the lateral direction presented by Eq. (3) will be a delta function, which is shown as an arrow in FIG. 2A. However, in real situations, the imaging sample may be optically heterogeneous, which means that a(z,t) and n are functions of the time variable t. Thus, Eq. (3) may be expressed as:

$$I(k_j,t)=2S(k_j)E_R\int_{-\infty}^{\infty}a(z,t)\cos(2k_jnz)dz \quad (4)$$

As a consequence, in various embodiments, Eq. (4) may not be constant anymore. In embodiments, the intensity captured by the CCD camera may be modulated by the heterogeneous properties of the sample along each B-scan. The spatial frequency components of a static tissue sample, which are referred to herein as the heterogeneous frequencies, may be exhibited as a randomly distributed function around zero frequency with a bandwidth (BW) as shown in the curve in FIG. 2B.

In various embodiments, such as when there is a patent blood vessel buried within a motionless tissue at position $(z_1,t_1)$, it may be assumed that the blood cells (e.g., the scattering particles) within the vessel may move toward the incident beam at a velocity v. The frequency of the light backscattered from these blood cells may be modulated by its velocity. Then, Eq. (4) may be expressed as:

$$I(k_j,t)=2S(k_j)E_R[\int_{-\infty}^{\infty} a(z,t)\cos(2k_jn(z,t)z)dz+a(z_1,t_1)\cos[2k_jn(z_1,t_1)(z_1-vt)]] \quad (5)$$

Figure 2:
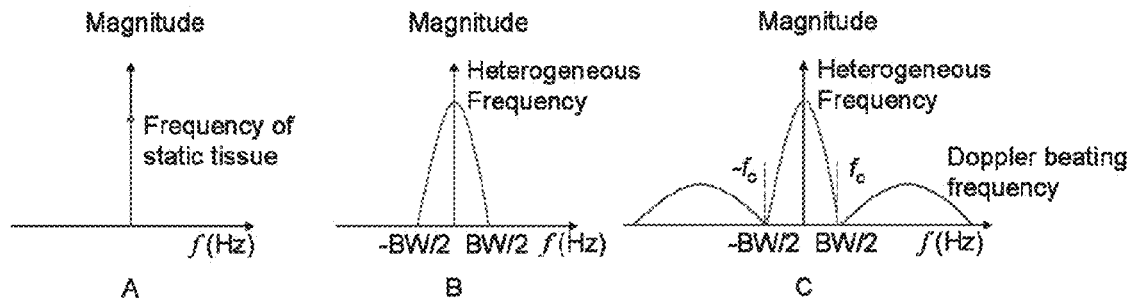
FIGS. 2A-C illustrate frequency components for different tissue samples: an ideal tissue sample (optically homogeneous sample) with no moving particles (FIG. 2A), a real tissue sample (optically heterogeneous sample) with no moving particles (FIG. 2B), and a real tissue sample (optically heterogeneous sample) with moving particles (FIG. 2C), in accordance with various embodiments.

In this embodiment, the self cross-correlation signal from within the sample is also not considered. The 1$^{st}$ term on the right side of Eq. (5) represents backscattering signals from a static sample with reflectivity of $a(z,t)$, while the 2$^{nd}$ term represents backscattering from the moving particles with reflectivity of $a(z_1,t_1)$ with a velocity of v at position $(z_1,t_1)$. In various embodiments, moving particles may produce a frequency shift caused by the Doppler effect of the moving particles. This is illustrated in FIG. 2C, where the second curve is the Doppler beating frequency part. As discussed, the phase-resolved technique may require a correlation between neighboring A-scans to determine v of the moving particles, and the correlation, in conventional PRDOCT, provided by the 1$^{st}$ term on the right-side of Eq. (5) also may be required to suppress the noise signals in the non-flow regions in order to increase the flow imaging contrast. Because of the optical heterogeneity $n(z,t)$ of a tissue, $n(z,t)$ may impose a noise background onto the blood flow signals, making it difficult for PRDOCT to measure precisely the blood flow velocity, particularly in capillaries. In contrast, in embodiments, OMAG may eliminate the 1$^{st}$ term on the right side of Eq. (5) in order to image blood flow. This elimination may minimize or reduce the noise production due to $n(z,t)$, but may result in OMAG losing its correlation condition between neighboring A-scans for the heterogeneous tissue regions. Consequently, the phase-resolved technique may not be directly applied to OMAG blood flow signals. Thus, various embodiments may employ the strategy of digitally reconstructing an ideal sample background with a constant backscattering coefficient $a_0$ and a refractive index $n_0$ throughout the sample, as illustrated in Eq. (6)—thus creating a totally homogeneous sample which may reinforce a complete correlation among OMAG A-scan signals.

$$I(k_j,t)=2S(k_j)E_R\int_{-\infty}^{\infty} a(z,t)\cos(2k_jn_0(z,t)z)dz \quad (6)$$

where $a_0(z,t) \equiv a_0$ and $n_0(z,t) \equiv n_0$ throughout the scanned tissue sample. In embodiments herein, $a_0=10^{-6}$ and $n_0=1.35$ when constructing the homogenous tissue background using Eq. (6). These values are taken according to the typical optical properties of biological tissues, e.g., the average reflectivity may be between $10^{-4}$ and $10^{-7}$ and the average refractive index may be 1.35.

In various embodiments, the digitally reconstructed homogenous tissue sample may subsequently replace the first term on the right side of Eq. (5). In doing so, OMAG blood flow signal now becomes:

$$I'(k_j,t)=2S(k_j)\{E_R\int a_0 \cos(2k_jn_0z)dz+E_Ra(z_1,t_1)\cos[2k_jn(z_1,t_1)(z_1-vt)]\} \quad (7)$$

In various embodiments, the construction of the ideal tissue sample may not affect OMAG signals of blood flow because it may only replace the tissue background signals with a homogeneous background without affecting the blood flow signals within the B-scan. If the time variable t is treated as a constant and a Fourier transformation is applied upon wavelength k, then:

$$\tilde{O}(z,t)=FT^{-1}\{I(k_j,t)\}|_k=A(z,t)\exp[i\phi(z,t)] \quad (8)$$

where $\Psi(z, t)$ is the phase of the analytic signal. The phase difference between neighboring A-scans, n and n−1, is then evaluated:

$$\Delta\varphi(z, t) = \tan^{-1}\left[\frac{\text{Im}[\tilde{I}(z, t_n) \cdot \tilde{I}^*(z, t_{n-1})]}{\text{Re}[\tilde{I}(z, t_n) \cdot \tilde{I}^*(z, t_{n-1})]}\right] \quad (9)$$

Based on the linear relationship between phase difference between neighboring A-lines and velocity, the velocity of flow signal imaged by OMAG may be directly written as:

$$v(z, t) = \frac{\lambda\Delta\varphi(z, t)}{4\pi n\Delta t} \quad (10)$$

where $v(z,t)$ is the flow velocity at depth z, $\Delta t$ is the time interval between neighboring A-lines, and n is the refractive index of the sample. In embodiments, there may be a small constant offset induced by $a_0$ in Eq. (8), which may perturb the evaluated $\Delta\phi(z, t)$. However, the small offset is usually at least two orders of magnitude smaller than the OMAG flow signals, leading to a negligible effect on the final evaluated $\Delta\phi(z, t)$.

Figure 3:
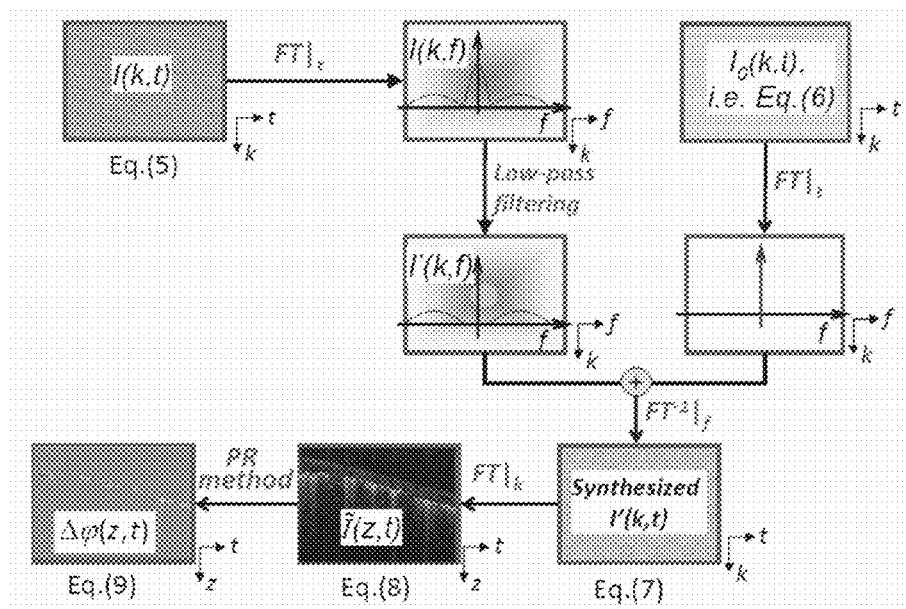
FIG. 3 is a flow chart showing the steps used in an example of Doppler optical microangiography (DOMAG) for evaluating the velocities of blood flow from a B-scan dataset, I(k,t), in accordance with various embodiments.

As disclosed herein, an InGaAs camera may be used in various embodiments to capture the interferograms at 31 KHz A-scan rate. Thus, the maximum detectable flow velocity that does not undergo phase-wrapping may be 10 mm/s for the OMAG system used (FIG. 1). In embodiments, the modulation frequency fc=400 Hz may be selected for OMAG to filter out the heterogeneous frequencies that represent the static tissue components. This value may be empirically determined from the tissue samples used, which may correspond to a minimal flow velocity of ~0.26 mm/s that may be detected by the system. FIG. 3 provides a flow chart illustrating how DOMAG works in some embodiments to obtain final velocity images of blood flow of the scanned tissue sample. The data coordinates are indicated in the lower right corner of each data block, where t is the time variable of probe beam scanning over a sample, k is the wavenumber, f is the spatial frequency, and z is the imaging depth. FT|$_t$ represents the Fourier transform (FT) against the time variable t in the B-scan, FT|$^{-1}$|$_f$ indicates the inverse FT against the spatial frequency, f, and FT|k is FT against the wavenumber k.

Figure 4:
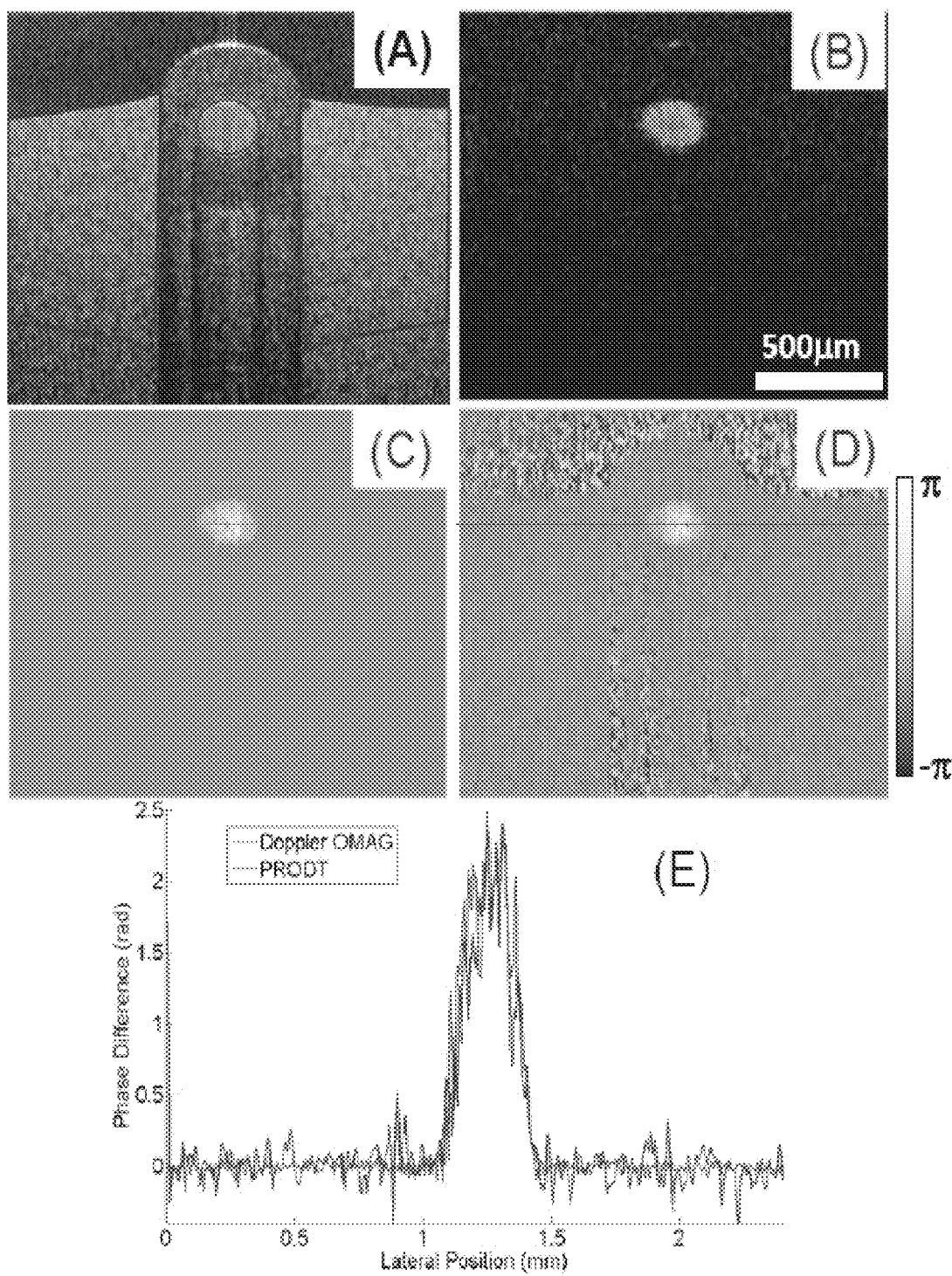
FIGS. 4A-E illustrate the results of various imaging techniques imaging on a flow phantom.

In various embodiments, to validate the efficacy of the disclosed method, the method was performed on a flow phantom. In one specific, non-limiting example, the phantom was made from gelatin mixed with 2% milk to simulate the background optical heterogeneity of the tissue in which a capillary tube with an inner diameter of about 200 μm was submerged and a ~2% $TiO_2$ particle solution was flowing in it. The inclining angle of the tube toward the incident beam, e.g., the Doppler angle, was set at about 85°. The flow rate of the particle solution was controlled by a precision syringe pump to a range that falls within the detectable range of the OMAG system, e.g., velocity between 0.2 and 10 mm/s. In this embodiment, each B-scan (lateral direction) contained 1000 A-lines covering 2.5 mm. Thus, the corresponding $\Delta x$ between neighboring A-lines was 2.5 μm. The results are shown in FIG. 4.

FIG. 4A shows the OMAG structural image of the scanned tissue phantom that is identical to the image obtained by conventional SDOCT, while the corresponding OMAG flow image is shown in FIG. 4B. It can be seen that OMAG successfully delineates the fluid flow within the capillary tube with the background signals from the non-flow region of phantom being rejected. However, OMAG does not provide the velocity information of flowing particles within the capillary tube. The fluid flow velocity information was then evaluated by DOMAG as described in Section 3 (FIG. 4C), and PRDOCT (FIG. 4D) methods, respectively.

In various embodiments, it is clear that DOMAG provides superior imaging performance because the background phase noise is maximally suppressed in FIG. 4C as compared to FIG. 4D. In embodiments, the phase noise suppression may occur in the entire output plane due to the digital reconstruction of the ideal tissue phantom in DOMAG. This may be advantageous because it is not necessary to use a segmentation method to segment the tissue regions of interest so as to exclude low signal regions when evaluating useful flow velocity signals, as is normally done in conventional PRDOCT. In embodiments, this may lead to a reduced demand for computing power.

To better show the noise suppression by DOMAG, FIG. 4E illustrates the signal profiles across the B-scan at the depth positions marked in FIGS. 4C and 4D, respectively. The curve was extracted from the locations marked with the line in FIG. 4C, while the curve indicates these same locations in FIG. 4D. In this embodiment, the phase differences caused by the flowing particles (e.g., the parabolic curve) were almost the same using these two methods, however the noise background in DOMAG is much smaller than that in PRDOCT.

In another embodiment, to quantitatively evaluate the improvement provided by DOMAG, the flow velocity signals were calculated, as well as the phase noise levels. Two regions were defined from the structural image (FIG. 4A): flow signal region $\Omega^S$, marked as the circle, and noise region $\Omega^N$, enclosed by the lines. The flow signal region was determined by segmenting the lumen of the capillary tube, while the noise region was determined by segmenting the micro-structural signals from the structural image of the scanned phantom. The segmentations were straightforward because in this simple embodiment, it was known where the flow was located. Two masks were produced from the resulting two regions, and were used in combination with the DOMAG image (FIG. 4C) and PRDOCT image (FIG. 4D) to calculate the phase signals in the respective regions. In some embodiments, it is not necessary to perform the segmentation to evaluate the phase noise in DOMAG, however, to make it a fair comparison between DOMAG and PRDOCT, the phase differences within exactly the same regions were evaluated for both the methods.

The phase noise level in the velocity image was calculated by evaluating the standard deviation of the phase differences, $\Delta\phi$, between neighboring A-lines within region $\Omega^N$, $$\sigma_{\Delta\varphi} = \sqrt{\frac{1}{M-1}\Sigma_{\Omega^N}(\Delta\varphi - \overline{\Delta\varphi})^2} \quad (11)$$

where M is the total number of pixels within the region $\Omega^N$. $\overline{\Delta\phi}$ is the average value of the phase differences $\Delta\phi$. The useful flow signals were defined by following algorithm in the flow region $\Omega^S$:

$$S = \Sigma_{\Omega^S}(\Delta\phi > \sigma_{\Delta\phi}) \times \Delta\phi \quad (12)$$

where the bracket term represents a binary operation for which it returns 1 if $\Delta\phi$ is larger than $\sigma_{\Delta\phi}$, or else it returns to 0. In doing so, the value S represents the effective detectable signals that are treated as useful signals of flow velocities for the target flow. Finally, the phase SNR may be defined by:

$$\text{Phase SNR} = 20 \times \log(S/\sigma_{\Delta\phi}) \quad (13)$$

In various embodiments, the phase SNR indicates a metric for imaging contrast, rather than the phase sensitivity of the system used. In embodiments, the phase sensitivity for both DOMAG and PRDOCT may generally be the same, which is determined by the system setup and the beam scanning pattern over the sample.

The results are tabulated in Table 1 for both the OMAG and PRDOCT methods. In this example, compared to PRDOCT, the phase noise $\sigma_{\Delta\psi}$ was reduced from 0.43 rad to 0.037 rad for DOMAG, which represents a more than 11-fold improvement. The detectable effective velocity signals were also improved, from 4198 to 4395. Consequently, the phase SNR was increased by 22 dB, from 79 dB to 101 dB.

TABLE 1

Evaluated phase noise, effective signal and phase SNR of phase differences for DOMAG and PRDOCT

| | $\sigma_{\Delta\phi}$ | S | Phase SNR |
|---|---|---|---|
| DOMAG | 0.037 rad | 4395 rad | 101 dB |
| PRDOCT | 0.43 rad | 4189 rad | 79 dB |
| Improvement | 11.6 (times) | 4% (unitless) | 22 dB |

From the above analyses, it is apparent that the noise level in DOMAG may be greatly reduced. In PRDOCT, the phase noise level is often termed as the phase sensitivity, which can be determined by the intensity signal to noise ratio of the OCT system, X, by the following equation:

$$\sigma_{\Delta\varphi}^2 = \left(\frac{1}{X}\right) \quad (14)$$

In various embodiments, the phase sensitivity value calculated from Eq. (14) represents the upper limit that the phase resolved method can achieve under the total correlation condition between neighboring A-scans, which might be met in PRDOCT by repeated A-scans at the same sample position. For the examples described herein, the OCT intensity SNR for the flow region was about 30 dB, which is quite common in the case of imaging in vivo. Thus, the corresponding phase sensitivity was about 0.0316 rad. Thus, the phase sensitivity of DOMAG evaluated through the B-scan was quite close to that of PRDOCT evaluated from the repeated A-scans at the same sample position, demonstrating the power of the disclosed DOMAG method for in vivo imaging of blood flow within the microcirculatory tissue beds.

In various embodiments, in vivo tests were performed to validate the efficacy of DOMAG for non-invasive assessment of microcirculation within tissue beds. In embodiments, the capability of DOMAG to image the cerebral blood perfusion in mouse models was demonstrated with the skull left intact. The mouse brain was selected for use in part because the brain is one of the least accessible organs for non-invasive observations of blood perfusion (as in the human brain). The 3-month old adult mouse, weighing about 25 g, was shaved to remove hair from the head before optical imaging. The mouse was then anesthetized by using 2% isoflurane (0.2 L/min $O_2$, 0.8 L/min air), and positioned in a stereotaxic stage to minimize movement. The body temperature was kept at about 37° C. Before the OMAG data acquisition, a window on the head was carefully made by removing the overlaying skin to allow OMAG imaging of the cerebral blood flow within the cortex through the intact skull. The exposed skull was washed by saline to prevent it from dehydrating. The whole imaging session lasted about 30 minutes, including about 25 seconds for optical imaging data acquisition.

Figure 5:
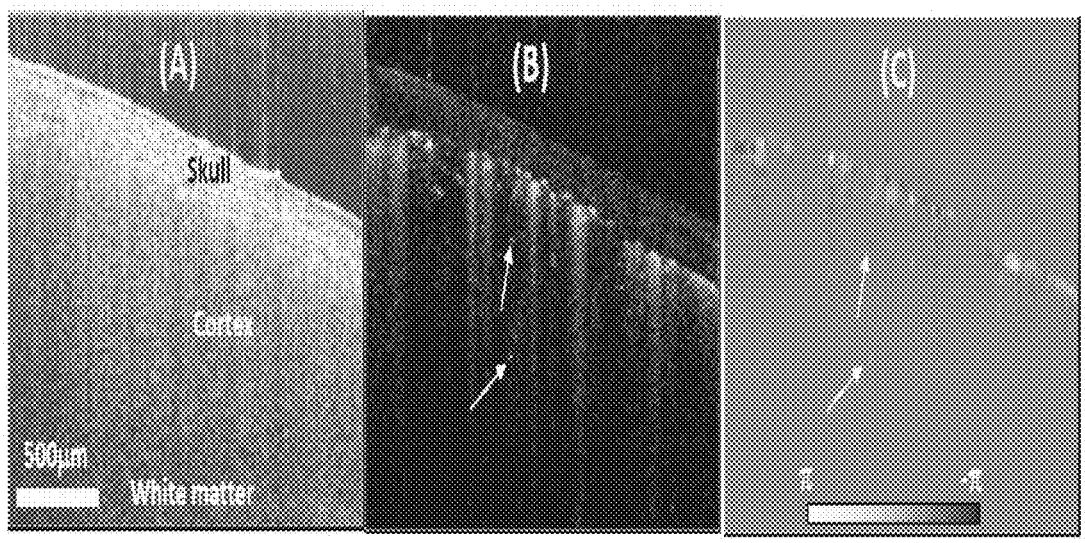
FIGS. 5A-C illustrate in vivo OMAG imaging results for an example of a typical B-scan of a mouse brain with the skull left intact.

Shown in FIG. 5 are the representative results from a single B-scan (frame) of a mouse brain. FIG. 5A is the OMAG structural image, identical to the cross-sectional image obtained from conventional SDOCT, from which the important histological layers were clearly delineated, including the cranium (skull), gray matter (cortex) and white matter. FIG. 5B shows the corresponding OMAG image of localized blood flow that permeates this cross-section (FIG. 5A). However, this image only provides the backscattered signals from functional blood that does not indicate the flow velocity information, which is needed for quantifying blood perfusion. Applying the DOMAG method, the velocity information as to the imaged blood flow may be extracted from FIG. 5B. The result is given in FIG. 5C, which represents an image of the DOMAG phase differences, $\Delta\phi(x, z)$ that may be converted to the velocity values by Eq. (10). The blood flow velocity in capillaries (indicated by white arrows, for example) is imaged by DOMAG.

In various embodiments, the 3D imaging in the OMAG system was achieved by scanning the focused sample beam over the skull using the X-Y scanner (FIG. 1). The field of view for the system was 2.5 mm by 2.5 mm (x-y), which contained 1500 A-scans in the x-direction (B-scan) and 500 B scans in the y-direction (C-scan). The original raw data cube (spectral interferograms) was first processed frame by frame, and then the resulting images, including structural, flow and velocity images, were recombined to produce 3D volumetric visualization of the scanned tissue volume.

Figure 6:
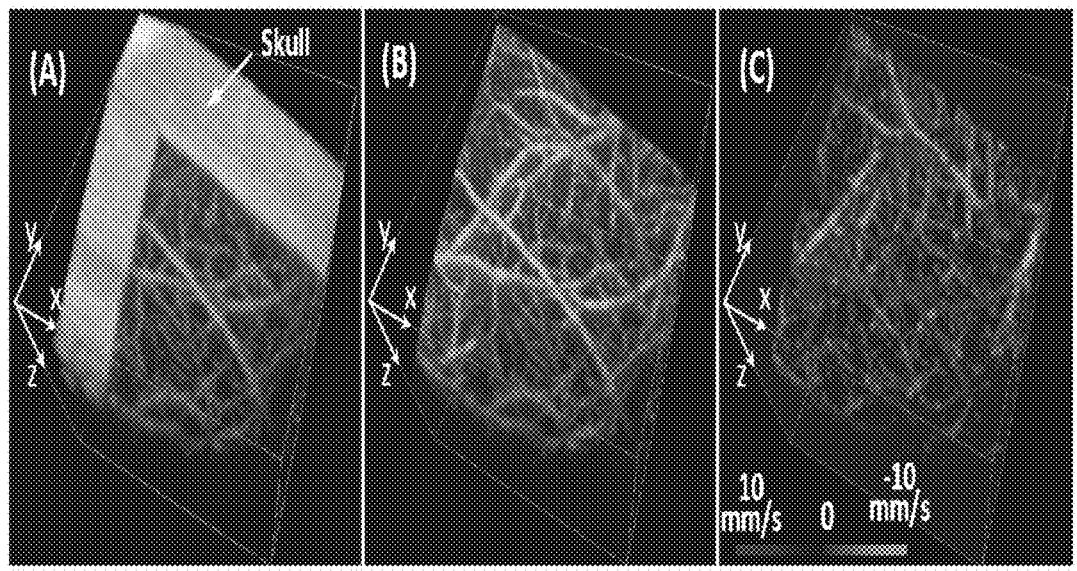
FIGS. 6A-C illustrate in vivo 3D OMAG imaging of the cortical brain of a mouse with the skull left intact; the volumetric visualization was rendered by merging the 3D microstructural image with the 3D cerebral blood flow image (FIG. 6A), the 3D signals of cerebral blood flow only (FIG. 6B), and the corresponding DOMAG imaging of velocities (FIG. 6C) within the 3D blood flow network in FIG. 6B, in accordance with various embodiments.

The results for an example of a typical tissue volume of 2.5×2.5×2.0 mm$^3$ are given in FIG. 6. FIG. 6A is a volumetric visualization rendered by merging the micro-structural 3D image (via SDOCT) with the corresponding 3D image of functional blood flows (via OMAG), where the precise locations of blood flow may be identified within microstructures of the sample. In the image, a cutaway view is used to appreciate how the blood vessels innervate the tissue volume. FIG. 6B shows the volumetric network of patent blood vessels within the scanned tissue volume, where the smallest diameter of blood vessels was identified at about 15 μm, close to the system spatial resolution (about 16 μm). The corresponding velocity information for the imaged blood flows is shown in FIG. 6C, evaluated by use of DOMAG. In FIG. 6C, the directional flow information is indicated. The physical image size was 2.5×2.5×2.0 (x-y-z) mm$^3$.

Figure 7:
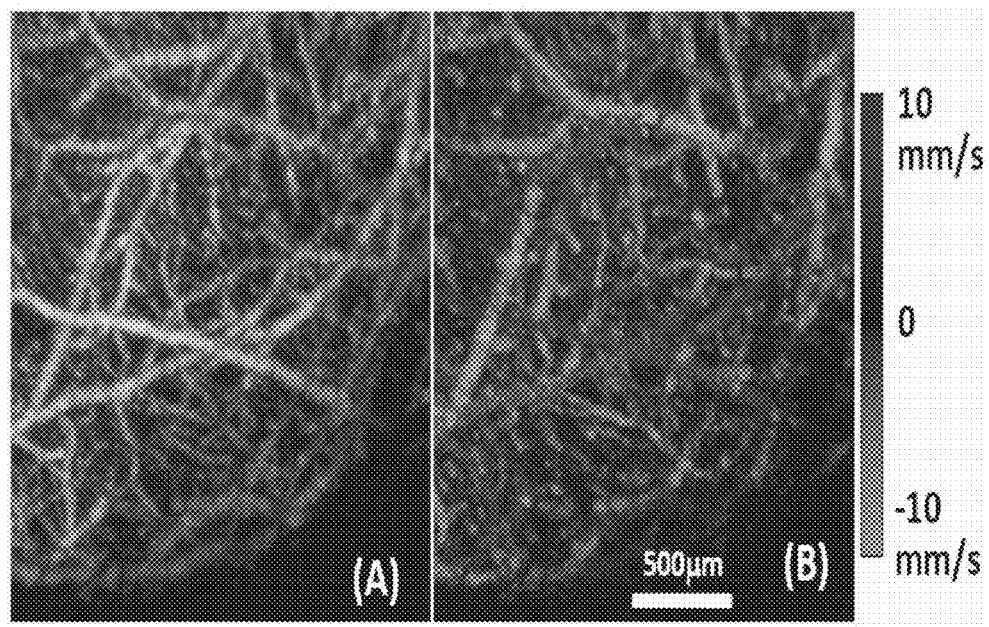
FIGS. 7A and 7B illustrate a maximum projection view (x-y) of OMAG (FIG. 7A) and DOMAG (FIG. 7B) of the cerebral blood flow in the cortical brain of the mouse shown in FIG. 6, in accordance with various embodiments.

To show in detail the blood vessel networks and blood flow velocities within them, the maximum projection approach was used to obtain x-y projection images. Together with the blood vessel perfusion networks (FIG. 7A), Doppler OMAG (FIG. 7B) provides a powerful tool to quantify blood perfusion within the microcirculation tissue beds in vivo.

Figure 8:
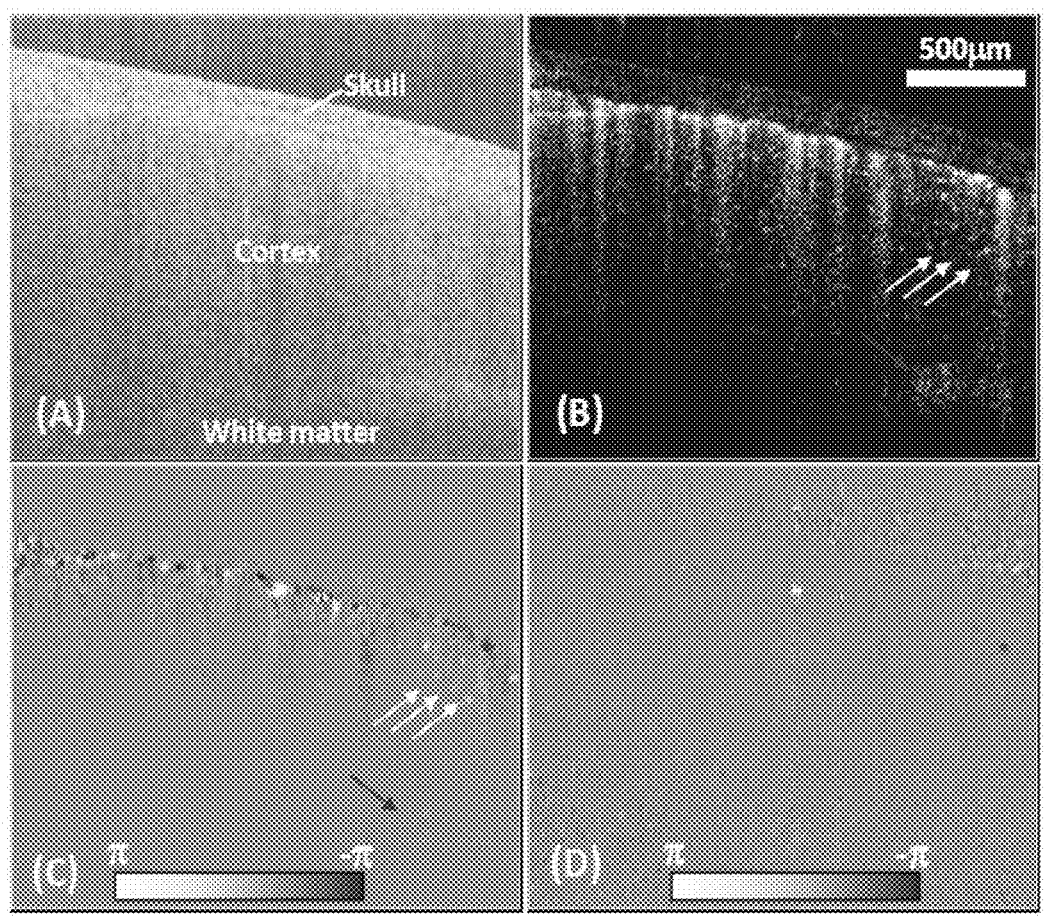
FIGS. 8A-D illustrate a comparison between OMAG and PRDOCT B-scan imaging of the cortical brain in mice in vivo: OMAG structural image (e.g., SDOCT.

Because both the DOMAG and PRDOCT methods are capable of providing the velocity information for the blood flows within the living biological tissue, a comparison between these two techniques for in vivo imaging is provided. In embodiments, the final imaging results may be different under different system setups, for example for the imaging speed and the number of A-scans used in a single B-scan. Thus, for a fair comparison, the same data set was used for each, which was obtained from a mouse brain with the skull left intact under the same system configurations. For this set of embodiments, the imaging speed was 20 KHz A-scan rate. FIG. 8 shows the results from an example of a typical B-scan obtained from the cortical brain of a mouse. The OMAG method obtained the images of microstructures via SDOCT (FIG. 7A), blood flow via OMAG (FIG. 8B) and the corresponding velocities of blood flow via DOMAG (FIG. 8C). DOMAG calculated the velocities of blood flow in functional vessels, including capillaries (white arrows for example), and even in the vessels about 1.5 mm deep below the bone surface (arrow). However, the PRDOCT result (FIG. 8D) indicated that conventional DOCT failed to provide detailed velocities of blood flow in this case. In embodiments, the level of background phase-noise may be an important metric when quantifying blood flow, particularly in capillaries, because this metric affects the ability to extract useful flow signals from the noisy background. Using the method described above, the noise level for PRDOCT was typically 0.5 rad, largely due to the heterogeneous property of the tissue sample as seen in FIG. 8D, indicating that PRDOCT may not be able to measure blood flow velocities less than 1.1 mm/s when the A scan rate is at about 20 kHz. However, DOMAG was able to reduce this noise level to 0.034 rad, which is comparable to the phantom experiments shown above, indicating an approximate 15-fold improvement in imaging blood flow velocities over conventional PRDOCT. Thus, DOMAG provides a good tool for quantifying blood flow within a perfused tissue.

Figure 9:
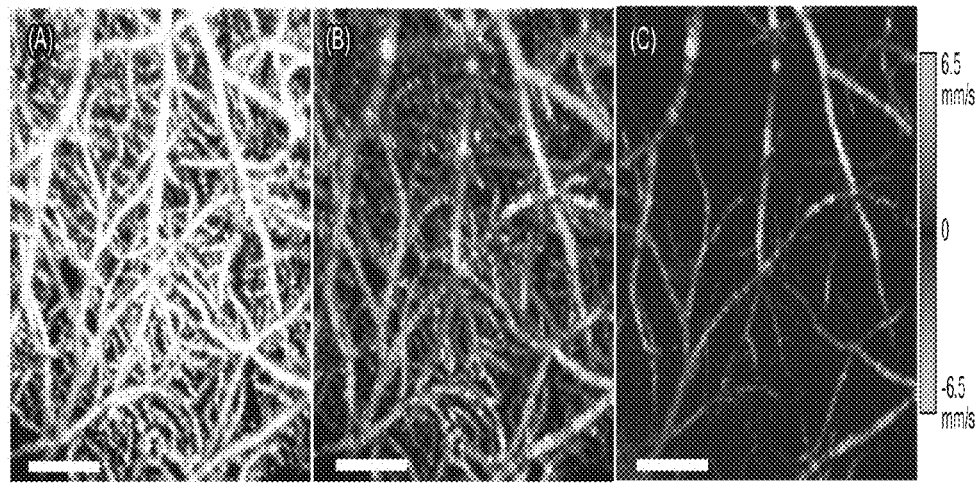
FIGS. 9A and B illustrate a comparison between 3D OMAG and PRDOCT imaging of the cortical brain in mice with the intact skull in vivo, showing the maximum x-y projection views of an OMAG cerebral blood flow image (FIG. 9A), a DOMAG flow velocity image (FIG. 9B), and a PRDOCT flow velocity image (FIG. 9C), in accordance with various embodiments.

To further demonstrate the advantages of DOMAG in imaging blood flow velocities, 3D DOMAG and PRDOCT images were compared and evaluated from a scanned tissue volume from the mouse brain cortex with the skull left intact. FIG. 9 (shown as projection images to x-y) illustrates the difference between OMAG, DOMAG, and PRDOCT imaging of cerebral blood flow in mice under the same conditions. To obtain the PRDOCT flow image, algorithms were used to reduce the noise artifacts; algorithms for minimization of the sample motion artifacts, segmentation of regions of interest and correction of phase-wrapping errors were implemented. It did not require performing the segmentations in DOMAG in order to render the 3D image as the phase noise level was low in the entire 3D space. The physical size of scanned tissue volume was 2.5×2.5×2.0 mm$^3$. The white bar=500 μm.

These results indicate that DOMAG (FIG. 9B) reliably determined the velocities of blood flows within almost all vessels in the scanned tissue. Not surprisingly, PRDOCT (FIG. 9C) may be erroneous in quantifying blood flows within the scanned tissue, due to noise produced in PRDOCT, which masks slow flows (<1.1 mm/s) in small vessels. Furthermore, blood vessel diameters seen in the DOMAG and OMAG images were significantly larger than those in the DOCT images, indicating a clear advantage of DOMAG over DOCT in quantifying blood flow in the scanned tissue.

In embodiments, the reason for these differences may be that the performance of conventional PRDOCT is limited by the background texture noise pattern caused by the optical heterogeneity, e.g., microstructures, of the tissue sample. By contrast, DOMAG uses an ideal reconstructed sample as the tissue background, which makes the neighboring OMAG A-scans totally correlated, maximally satisfying the correlation requirement for the phase-resolved technique. As a consequence, DOMAG may reduce the background phase noise to a minimum. In embodiments, this may improve the capability of DOMAG to detect low blood velocity near the wall of the blood vessel, and thus the diameter of blood vessels detected by DOMAG is larger than that detected by PRDOCT, as seen in FIG. 9.

Figure 10:
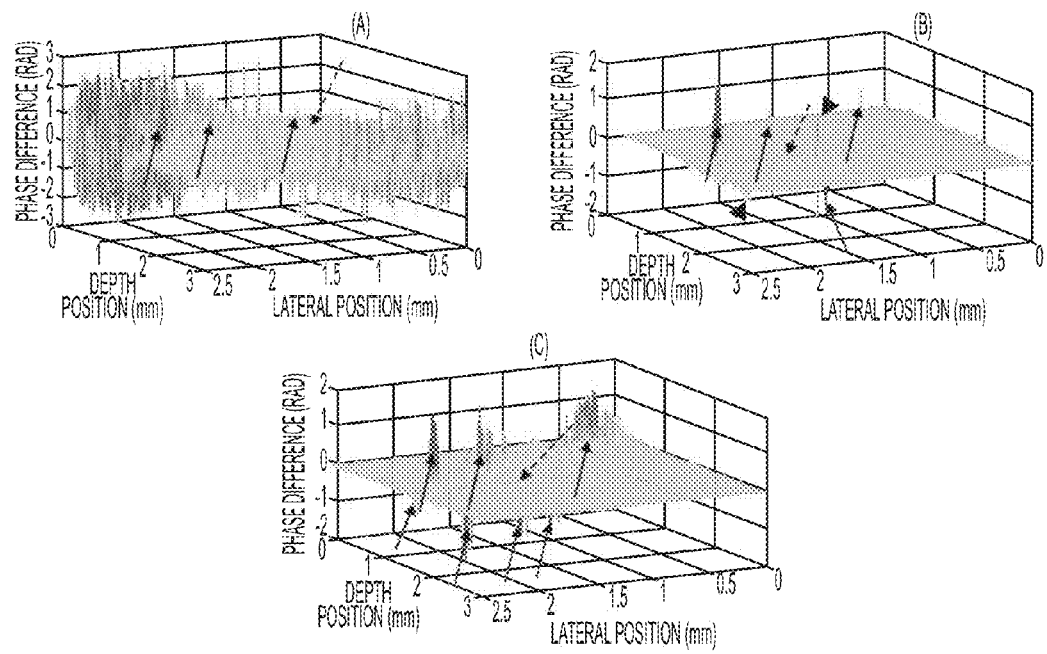
FIGS. 10A-C illustrate a 3D plot of an example of a typical B-scan of flow images.

In various embodiments, an alternative way to illustrate the phase noise levels is to use 3D plots of cross-sectional images (B-scans), e.g., FIG. 8. Shown in FIG. 10 is such an illustration for a typical B-scan from the cortical brain in mice. FIG. 9A shows a conventional PRDOCT flow velocity plot, without applying the segmentation approach to eliminate the random phases in low signal regions. The flow signals are indicated by the black arrows and the noise in useful signal region is indicated with a broken arrow. In the low OCT signal regions, for example the region above the tissue surface where there is no light reflectivity and the region deep in the tissue where the detected optical signal is low due to the light attenuation, the evaluated phases may exhibit random phase noise signals in PRDOCT.

From FIG. 10A, it is clear that the noise in the low-signal region overwhelmed the useful flow signals, thus segmentation is often needed in PRDOCT to exclude these random noises. After segmentation of the tissue region of interests, a better view is illustrated in FIG. 10B to show the effects of background noise in the tissue region. In FIG. 10B, the noise indicated with the broken arrow is so high that it prevents the small blood vessel signals from being detected. In particular, those indicated by arrow heads are difficult to distinguish from background noise. For DOMAG, shown in FIG. 10C, the background noise is very small compared to the blood vessel signals, which improves significantly the imaging performance for DOMAG.

Figure 11:
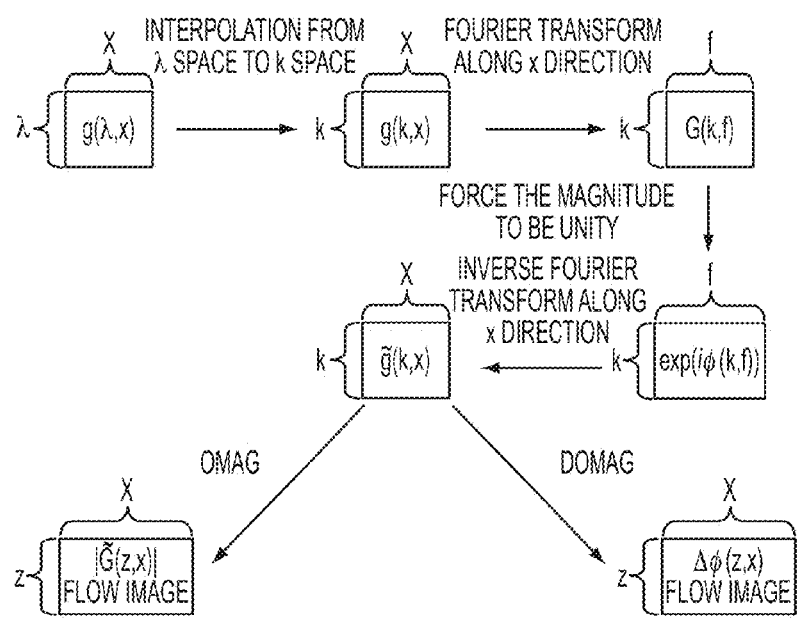
FIG. 11 illustrates a flow chart of an example of a phase-only filtering process, in accordance with various embodiments.

The disclosed embodiments also include another method of performing OMAG and quantifying blood flow using DOMAG. In various embodiments, this method uses a phase-only filter to detect the high frequency components, which corresponds to the Doppler shift caused by the particles movements. FIG. 11 provides a flow chart that illustrates the steps of the phase-only filter method. The spectral interferogram signals for each B-scan captured by the OMAG system are presented as $g(\lambda,x)$, where $\lambda$ is wavelength and x is the lateral position in the B-scan. This captured raw interferogram data $g(\lambda,x)$ is first interpolated into k space $g(k,x)$ along $\lambda$ direction column by column. In embodiments, to perform the phase-only filter process, the interpolated interference fringe data may be Fourier transformed along x direction row by row to obtain the frequency components. For all the frequency components, the magnitudes are forced to be unity, while the phases are left unchanged so that a phase image $\exp(i\phi(k,f))$ is obtained. After this, the phase data, $\exp(i\phi(k,f))$, may then be inverse Fourier transformed along the x-direction to obtain a set of filtered interferogram signals. In embodiments, these filtered interference signals mainly contain the high frequency components of the raw signals, while the low frequency components are suppressed. Based on these filtered signals, the OMAG method is further applied to abstract a flow image and obtain a flow velocity image using DOMAG.

Figure 12:
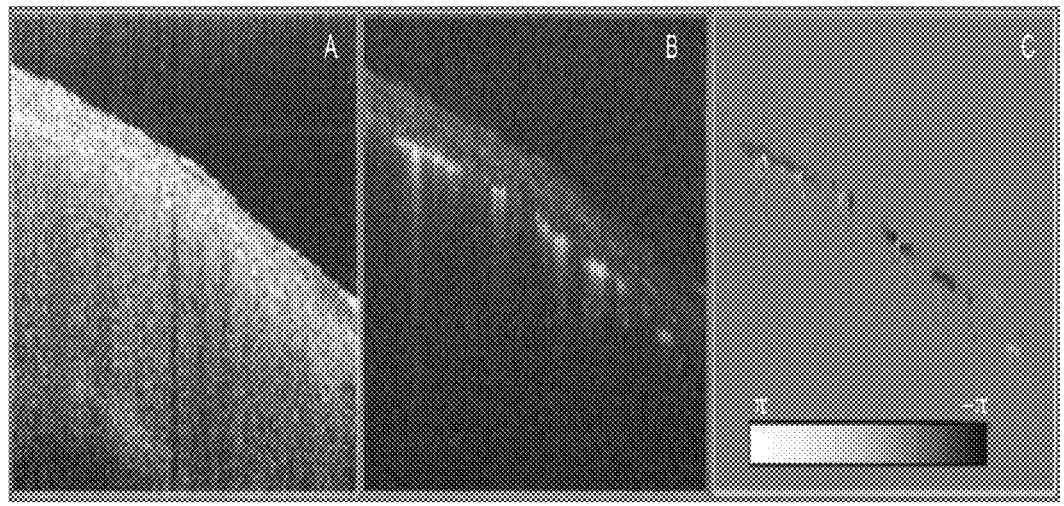
FIGS. 12A-C illustrate in vivo phase-only filtering imaging results for an example of a typical B-scan of a mouse brain.

FIG. 12 shows an example of typical results from a single B-scan of a mouse brain. FIG. 12A is the structure image, and FIG. 12B is the corresponding flow image obtained through phase-only filter described above. This image localized the optical signals that are backscattered from the functional blood vessels. To extract the velocity information, the DOMAG method was further applied to the filtered interference signal. The results are presented in FIG. 12C, which corresponds to the phase difference map obtained by DOMAG method, and can be converted to velocity image through the following equation:

$$v(z, t) = \frac{\lambda \Delta \varphi(z, t)}{4\pi n \Delta t} \quad (10)$$

In various embodiments, for other phase-sensitive OCT methods, for example optical coherence elastography, the phase difference map that represents the tissue motion may also have the same problem as stated above, e.g., the low level signals cause random phase noise. The random noise makes the current optical coherence elastography approach almost impractical for use on the tissue samples both in vivo and in vitro. Using the digital background reconstruction method described above, these random phase noises can be successfully eliminated, making a quantum step for optical coherence elastography from laboratory research to real clinical and in vivo applications.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A method of quantifying blood perfusion in a living tissue sample, comprising:
   obtaining an optical microangiography (OMAG) image of a sample, wherein the image has an OMAG background sample;
   digitally reconstructing a homogeneous ideal static background tissue;
   replacing the OMAG background sample with the digitally reconstructed homogeneous ideal static background tissue;
   correlating two or more neighboring A-lines with the digitally reconstructed homogeneous ideal static background tissue; and
   measuring a phase difference between the two or more neighboring A-lines to quantify blood perfusion in the sample.

2. The method of claim 1, wherein obtaining an OMAG image of the sample comprises:
   scanning the sample with an incident beam from a light source to generate two or more neighboring A-lines;
   detecting one or more spectral interference signals from the sample;
   modulating the one or more spectral interference signals while scanning the sample in a cross-sectional direction (B scan); and
   obtaining at least one image of the sample from the modulated one or more spectral interference signals, the at least one image including a selected one of a full range structural image of the sample, a separated structure/flow image of the sample, and a background sample.

3. The method of claim 2, wherein obtaining at least one image from the sample comprises:
   separating structure information of the sample and flow information of the sample; and
   obtaining a first image and a second image, the first image including the structure information and the second image including the flow information.

4. The method of claim 2, wherein scanning comprises scanning the sample with the incident beam in x and $\lambda$ directions to obtain a first two dimensional (2-D) spectral interferogram data set, said x direction including one or more columns and said $\lambda$ direction including one or more rows.

5. The method of claim 4, wherein obtaining the at least one image comprises:
   calculating discrete analytic functions, along the x-direction and row by row in the $\lambda$ direction of the first 2-D data set, to obtain a complex valued function of the first 2-D data set; and converting the complex valued function of the first 2-D data set from a spectral domain to a time domain, column by column in the x direction, to obtain the at least one image of the sample.

6. The method of claim 5, wherein calculating discrete analytic functions comprises Hilbert-transforming the first 2-D data set.

7. The method of claim 5, wherein converting the complex valued function of the first 2-D data set comprises Fourier-transforming the complex valued function of the first 2-D data set.

8. The method of claim 4, further comprising scanning the sample with the incident beam in the x and λ directions along y direction to obtain a second 2-D spectral interferogram data set, said first and second 2-D data sets forming a three-dimensional spectral interferogram data set.

9. The method of claim 2, wherein said obtaining at least one image comprises obtaining the separated structure/flow image of the sample, and wherein the flow image of the sample is indicative of a direction of flow of the sample.

10. The method of claim 1, wherein measuring the phase difference between the two or more neighboring A-lines to quantify blood perfusion in the sample comprises using a phase resolved technique to extract flow velocity information.

11. The method of claim 1, further comprising filtering the spectral interference signals for each B scan using a phase-only filter.

12. The method of claim 11, wherein filtering the spectral interference signals for each B scan using a phase-only filter comprises:
Fourier-transforming interpolated fringe data along an x direction to obtain frequency components;
forcing the magnitudes of the frequency components to be unity while leaving the phases unchanged; and
inverse-Fourier-transforming phase data along the x direction to obtain a filtered interferogram signal.

13. A method for quantifying blood perfusion in a sample, comprising:
scanning a flowing sample with an incident beam from a light source;
detecting one or more spectral interference signals from the flowing sample to generate an OMAG blood flow sample;
digitally reconstructing a homogeneous ideal static background tissue;
replacing a real background sample with the digitally reconstructed homogeneous ideal static background tissue;
correlating two or more neighboring A-lines with the digitally reconstructed homogeneous ideal static background tissue; and
measuring the phase difference between the two or more neighboring A-lines to quantify blood perfusion in the sample.

14. The method of claim 13, wherein digitally reconstructing a homogeneous ideal static background tissue comprises digitally reconstructing an ideal sample background with a constant backscattering coefficient $a_0$ and a refractive index $n_0$ throughout the sample according to the equation:

$$I_0(k_j,t)=2S(k_j)E_R\int_{-\infty}^{\infty}a_0(z,t)\cos(2k_jn_0(z,t)z)dz,$$

wherein $a_0(z,t)\equiv a_0$ and $n_0(z,t)\equiv n_0$ throughout the sample.

15. The method of claim 13, wherein an OMAG blood flow signal is defined as:

$$I'(k_j,t)=2S(k_j)\{E_R\int a_0 \cos(2k_jn_0z)dz+E_Ra(z_1,t_1)\cos[2k_j n (z_1,t_1)(z_1-vt)]\}.$$

16. The method of claim 15, further comprising:
treating t (the time variable) as a constant; and
performing a Fourier transformation upon k (wavelength) such that $$\tilde{I}(z,t)=FT^{-1}\{I(k_j,t)\}|_k=A(z,t)\exp[i\phi(z,t)]$$

wherein $\Psi(z, t)$ is a phase of an analytic signal.

17. The method of claim 16, further comprising evaluating a phase difference between neighboring A-scans, n and n−1, according to the equation:

$$\Delta\varphi(z, t) = \tan^{-1}\left[\frac{\text{Im}[\tilde{I}(z, t_n)\cdot \tilde{I}^*(z, t_{n-1})]}{\text{Re}[\tilde{I}(z, t_n)\cdot \tilde{I}^*(z, t_{n-1})]}\right].$$

18. The method of claim 17, further comprising generating a velocity of flow signal using the equation:

$$v(z, t) = \frac{\lambda\Delta\varphi(z, t)}{4\pi n\Delta t}$$

wherein v(z,t) is a flow velocity at depth z, wherein Δt is a time interval between neighboring A-lines, and wherein n is a refractive index of the sample.

19. A method of using digital reconstruction to reduce random phase noise in a phase-resolved Doppler OCT method, comprising:
scanning a flowing sample with an incident beam from a light source;
detecting one or more spectral interference signals from the flowing sample;
digitally reconstructing a homogeneous ideal static background tissue;
replacing a real Doppler OCT background sample with the digitally reconstructed homogeneous ideal static background tissue;
correlating two or more neighboring A-lines with the digitally reconstructed homogeneous ideal static background tissue; and
measuring a phase difference between the two or more neighboring A-lines to reduce random phase noise.

20. A system for in vivo imaging, comprising:
an optical coherence tomography apparatus; and
one or more processors coupled to the apparatus and adapted to cause the apparatus to:
scan a sample with an incident beam from a light source to generate two or more neighboring A-lines;
detect one or more spectral interference signals from the sample;
modulate the one or more spectral interference signals while scanning the sample in a cross-sectional direction (B scan);
obtain at least one image of the sample from the modulated one or more spectral interference signals, the at least one image including a selected one of a full range structural image of the sample, a separated structure/flow image of the sample, and a background sample;
digitally reconstruct a homogeneous ideal static background tissue;
replace the background sample with the digitally reconstructed homogeneous ideal static background tissue;
correlate the two or more neighboring A-lines with the digitally reconstructed homogeneous ideal static background tissue; and measure the phase difference between the two or more neighboring A-lines to quantify blood perfusion in the sample.

21. The system of claim 20, wherein the optical coherence tomography apparatus includes a reference arm including a mirror mounted on a modulating device for modulating the one or more spectral interference signals.

22. The system of claim 20, wherein the one or more processors are adapted to cause the apparatus to scan the sample with the incident beam in x and $\lambda$ directions to obtain a first two-dimensional (2-D) spectral interferogram data set, said x direction including one or more columns and said $\lambda$ direction including one or more rows.

23. The system of claim 22, wherein the one or more processors are adapted to cause the apparatus to obtain the at least one image by:

calculating discrete analytic functions, along the x-direction and row by row in the $\lambda$ direction of the first 2-D data set, to obtain a complex valued function of 20 the first 2-D data set; and converting the complex valued function of the first 2-D data set from a spectral domain to a time domain, column by column in the x direction, to obtain the at least one image of the sample.

* * * * *